United States Patent [19]

Hopper et al.

[11] Patent Number: 4,877,901
[45] Date of Patent: Oct. 31, 1989

[54] PROCESS FOR SYNTHESIZING N,N'-DITHIOBIS(SULFONAMIDES)

[75] Inventors: Roger J. Hopper; Niranjan V. Shah, both of Akron; Steven M. Ryba, Norton, all of Ohio

[73] Assignee: The Goodyear Tire & Rubber Company, Akron, Ohio

[21] Appl. No.: 263,836

[22] Filed: Oct. 28, 1988

[51] Int. Cl.$^4$ .......................................... C07C 143/75
[52] U.S. Cl. ........................................ 564/82; 540/480; 540/596; 544/78; 546/186; 548/518
[58] Field of Search ............................ 564/82; 544/78; 546/186; 548/518; 540/480, 596

[56] References Cited

U.S. PATENT DOCUMENTS

| | | | |
|---|---|---|---|
| 3,400,152 | 9/1968 | Block et al. | 564/82 |
| 3,856,762 | 12/1974 | Hopper et al. | 546/186 |
| 3,898,205 | 8/1975 | Hopper et al. | |
| 3,898,206 | 8/1975 | Hopper et al. | |
| 3,904,664 | 9/1975 | Shelton et al. | 546/186 |
| 3,915,907 | 10/1975 | Hopper | |

FOREIGN PATENT DOCUMENTS 951719 10/1956 Fed. Rep. of Germany .
1101407 3/1961 Fed. Rep. of Germany .
1156403 10/1963 Fed. Rep. of Germany .

*Primary Examiner*—Donald G. Daus
*Attorney, Agent, or Firm*—Bruce J. Hendricks

[57] ABSTRACT

The present invention relates to a process for synthesizing N,N'-dithiobis(sulfonamides) by reacting a sulfonamide of the formula:

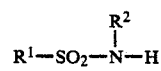

with sulfur monochloride and caustic in a mixed organic-aqueous media, wherein $R^1$ and $R^2$ are independently selected from the group consisting of alkyl radicals having from about 1 to about 20 carbon atoms, cycloalkyl radicals having from about 5 to about 20 carbon atoms, phenyl radicals, alkaryl radicals having from about 7 to 20 carbon atoms, and haloaryl radicals having about 6 to about 10 carbon atoms and where $R^1$ is also selected from radicals having the formula:

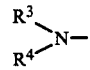

wherein $R^3$ and $R^4$ are individually selected from said alkyl, cycloalkyl, phenyl, alkaryl and haloaryl radicals and wherein $R^3$ and $R^4$ can be joined together to represent radicals selected from $-(CH_2)_n-$, where n is an integer of 4 to 7 and $-(CH_2)_2-O-(CH_2)_2-$.

14 Claims, No Drawings

PROCESS FOR SYNTHESIZING N,N'-DITHIOBIS(SULFONAMIDES)

FIELD OF THE INVENTION

The present invention relates to a process for the synthesis of N,N'-dithiobis(sulfonamides). The synthesis is conducted in a mixed organic-aqueous media.

BACKGROUND OF THE INVENTION

N,N'-dithiobis(sulfonamides) are useful in the preparation of N-chlorothiosulfonamides. For example, West German Pat. No. 1,101,407 discloses the preparation of N-chlorothiosulfonamides from N,N'-dithiobis (sulfonamides). As disclosed in U.S. Pat. No. 3,915,907, N-chlorothiosulfonamides are particularly useful as a rubber additive. Since the issuance of 3,915,907, the demand for N-chlorothiosulfonamides has been increasing and extensive research has been conducted to find an economical method of producing N-chlorothiosulfonamides.

West German Pat. No. 951,719 teaches a method of preparing N,N'-dithiobis(sulfonamides) by reacting anhydrous N-sodio-sulfonamides with sulfur monochloride. The process is conducted in an anhydrous organic media which unfortunately involves a high cost of production.

In view of the increasing demand for N,N'-dithiobis (sulfonamides) and the high cost of their production, there is a substantial need for a cheaper method for producing N,N'-dithiobis(sulfonamides).

SUMMARY OF THE INVENTION

There is disclosed a process for synthesizing N,N'-dithiobis(sulfonamides) comprising reacting a compound of the formula:

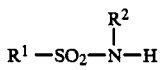
(I)

with sulfur monochloride and caustic in a mixed organic-aqueous media, wherein $R^1$ and $R^2$ are independently alkyl radicals having from about 1 to about 20 carbon atoms, cycloalkyl radicals having from about 5 to 20 carbon atoms, phenyl radicals, and alkaryl radicals having from about 7 to 20 carbon atoms, and haloaryl radicals having about 6 to about 10 carbon atoms and where $R^1$ is also selected from radicals having the formula:

wherein $R^3$ and $R^4$ are individually selected from said alkyl, cycloalkyl, phenyl, alkaryl and haloaryl radicals and wherein $R^3$ and $R^4$ can be joined together to represent radicals selected from $-(CH_2)_n-$, where n is an integer of 4 to 7 and $-(CH_2)_2-O-(CH_2)_2-$.

DETAILED DESCRIPTION OF THE INVENTION

The present invention relates to a new and improved process for synthesizing a N,N'-dithiobis(sulfonamide) of the formula:

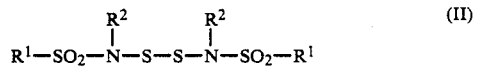
(II)

wherein $R^1$ and $R^2$ are independently alkyl radicals having from about 1 to about 20 carbon atoms, cycloalkyl radicals having from about 5 to 20 carbons atoms, phenyl radicals and alkaryl radicals having from about 7 to 20 carbon atoms, and haloaryl radicals having about 6 to about 10 carbon atoms and where $R^1$ is also selected from radicals having the formula:

wherein $R^3$ and $R^4$ are individually selected from said alkyl, cycloalkyl, phenyl, alkaryl and haloaryl radicals and wherein $R^3$ and $R^4$ can be joined together to represent radicals selected from $-(CH_2)_n-$, where n is an integer of 4 to 7 and $-(CH_2)_2 O-(CH_2)_2-$. Preferably, $R^1$ is a phenyl or tolyl radical and $R^2$ is an alkyl radical having from about 1 to 4 carbon atoms.

N,N'-dithiobis(sulfonamides) are derived from a sulfonamide compound of the formula:

(I)

wherein $R^1$ and $R^2$ are as described above. The sulfonamide of formula I may be prepared by reacting an aliphatic or aromatic primary amine with an aliphatic or aromatic sulfonyl chloride.

The sulfonamide of formula I is reacted with caustic to form the salt of the sulfonamide. Preferably the caustic is added in an aqueous solution. The caustic solution should not exceed a 70% concentration, with a concentration of 35% being preferred. For purposes of the present invention, the term "caustic" is intended to include sodium hydroxide, potassium hydroxide, or mixtures thereof. The amount of caustic preferably in solution should equal at least the molar amount of the sulfonamide of formula I. Therefore, the molar ratio of caustic to the sulfonamide may range from about 1:1 to 1.5:1. Preferably, the molar ratio caustic to the sulfonamide ranges from about 1:1 to 1.1:1.

The sulfonamide salt is formed and reacted with sulfur monochloride in the presence of a mixed organic-aqueous media. For ease of handling, it may be desirous to dissolve the sulfur monochloride in an organic solvent. Preferably, the organic solvent is the same as used for the reaction medium. The molar ratio between the sulfonamide salt and sulfur monochloride may vary. For example, molar ratios of the sulfonamide salt to sulfur monochloride may range from about 2:1 to 2.5:1, with a range of about 2.005:1 to about 2.05:1 being preferred.

In carrying out the process of the present invention, the pH of the reaction mixture should preferably remain neutral to alkaline. Alkalinity may be insured by maintaining a slight stoichiometric excess of caustic or sodium sulfonamide over sulfur monochloride as indicated in the preferred ranges above.

The order of addition of the reagents to the reaction mixture may vary. For example in one embodiment, all of the caustic may be added to the reactor with the sulfur monochloride being added later. According to another embodiment, the caustic and sulfur monochloride may be added in an alternating and intermittent manner. In yet another embodiment, which is also the most preferred, the flow of the caustic is initiated and then the flow of the sulfur monochloride is initiated so that both reagents are simultaneously introduced with sufficient excess of the caustic to maintain an alkaline pH throughout the course of the reaction and in the final reaction mixture.

The reaction media used in the process of the present invention comprises a mixture of an organic and aqueous media. Illustrative of organic solvents suitable for use in the practice of this invention include: benzene, chlorobenzene, toluene, ethylbenzene, n-propylbenzene, isobutylbenzene, xylene, and mixtures thereof. The preferred organic solvents are benzene, toluene and xylene. The weight ratio of organic to aqueous media may vary widely in accordance with the present invention. Generally, the weight ratio of total organic to total aqueous media ranges from about 7:1 to about 1:1 with a range of from about 6:1 to about 2:1 being preferred. Obviously, the solvents may be charged to the reactor separately or in combination with one or more of the reagents.

The amount of the organic media should be present in the reaction mixture in an amount sufficient to dissolve all the product at the reaction temperature. The amount of aqueous media should be sufficient to dissolve all the by-product salts that are formed during the reaction. Generally speaking, an amount of from about 100 to about 500 weight percent organic phase relative to the sulfonamide has been found sufficient for use in carrying out the present invention. An amount of from about 20 to about 95 weight percent aqueous phase relative to the sulfonamide has been found to be sufficient.

The process of the present invention may be carried out at a temperature ranging from about 20° C. to about 80° C. Preferably, the reaction temperature will range from about 40° C. to about 60° C.

As one skilled in the art can appreciate, the present invention may be carried out under a wide range of pressures. Generally speaking, the process of the present invention is carried out at atmospheric pressure.

Upon completion of the reaction, the product may be separated by one of several techniques as illustrated in the examples. Generally for single, isolated preparations, it is preferable to first separate the alkaline aqueous phase (containing inorganic salts and any unreacted sulfonamide salt) from the organic phase. The organic phase (containing dissolved product) may then be washed with water and, optionally, dilute mineral acid (as HCl, $H_2SO_4$) to ensure removal of all alkalinity. The product may be isolated from the organic phase by conventional means such as stripping solvent, cooling to precipitate, or precipitating by addition of a non-solvent. Use of the term "non-solvent" is intended to include an organic solvent miscible with the organic media used in the reaction and which when added lowers the solubility of the product. Suitable examples of such non-solvents include $C_5$-$C_{10}$ aliphatic hydrocarbons to name a few. For sequential batchwise preparations, it is desirable to recycle the solvent and any unreacted sulfonamide. In this case, it is preferable to first add dilute mineral acid to lower the pH of the reaction mixture to the neutral to acidic range, then separate the aqueous phase (containing inorganic salts). The organic phase may then be cooled to precipitate product. The product may be recovered by filtration and the filtrate (organic solvent containing unreacted sulfonamide) recycled to the next batch. In accordance with the embodiment where the caustic and sulfur monochloride are simultaneously introduced to the reactor, the product is preferably removed by cooling to precipitate In accordance with the embodiment where all of the caustic is added to the reactor with the sulfur monochloride being added later to the reactor, the product is preferably removed from solution by precipitation by addition of a non-solvent.

The reaction vessel should be equipped with a means of agitation, an inlet for the introduction of the reactants and a means of controlling temperature, e.g., cooling and heating means. Preferably, the reactor should be glass or other inert material to minimize corrosion effects of the reactants.

Practice of this invention is further illustrated by reference to the following examples which are intended to be representative rather than restrictive of the scope of the preset invention. Properties of the final products, expressed as weight percent were determined by liquid chromatographic analysis.

EXAMPLE 1

Preparation of
N,N'-dimethyl-N,N'-dithiobis(p-toluenesulfonamide)

The reaction vessel was a one liter, 4-necked, jacketed glass resin kettle with a bottom drain, fitted with a paddle stirrer, thermometer, two interchangeable addition funnels and a vent. To this reactor was added 220 grams (1.28 mole) N-methyl-p-toluenesulfonamide and 440 ml of toluene. The resulting slurry was stirred and 30 ml of water and 48 grams (1.2 mole) of sodium hydroxide pellets dissolved in 50 ml of water were added via an addition funnel. The addition was carried out over 20 minutes, during which the reactor temperature rose from 25° C. to 43° C. When addition was complete, 10 ml of water were rinsed through the funnel and into the reactor. Steam was passed through the reactor jacket to heat the stirred slurry to approximately 60°–70° C. for 15 minutes to insure that all of the caustic solution had reacted to form the sodium salt of N-methyl-p-toluenesulfonamide. Next, the reaction mixture was cooled to 25° C. by passage of cold water through the jacket. A solution of 78.4 grams (0.58 mole) of sulfur monochloride in 120 ml toluene was added via a second addition funnel. The addition was carried out over 30 minutes, the first ten minutes at 25°–30° C., and the remainder at 35°–40° C. The mixture was subsequently stirred 30 minutes at 35°–40° C. The reaction mixture was then subjected to four aqueous washes, keeping the temperature at 35°–40° C., stirring each wash, allowing layers to separate, and removing the lower aqueous wash layer through the bottom drain. The four aqueous washes were designed to remove unreacted N-methyl-p-toluenesulfonamide as the water soluble sodium salt and insure neutralization of any sodium hydroxide. The toluene (upper) layer was drained from the reactor into a 2 liter beaker, and mixed with 800 ml hexane to cause precipitation of a powdery white solid. The slurry was cooled to 25° C., filtered, washed with 50 ml hexane and dried at 50° C. 219 grams of N,N'-dimethyl-N,N'-dithiobis(p-toluenesulfonamide) having a melting point of about 90°–94° C. and 87 weight percent purity was obtained as a white powder.

EXAMPLE 2
Preparation of N,N'-dimethyl-N,N'-dithiobis(benzenesulfonamide)

The reactor was a 1 liter glass resin kettle equipped with a water jacket, bottom drain, and 4-necked head fitted with a paddle stirrer, thermometer, addition funnel and vent. The temperature was controlled by passing either cold water or steam through the jacket. During the procedure described below, nitrogen was occasionally blown up through the drain to mix the small dead volume which collected there. 172 g (1.0 mole) of N-methyl-benzenesulfonamide and 400 ml of toluene were added to the reactor and stirred to give a single liquid phase. A solution of 82 grams 50% aqueous sodium hydroxide in 40 ml of water (1.02 mole) was added via the addition funnel over 25 minutes with good stirring, causing a temperature rise from 25°–50° C. The resulting reaction mixture consisted of a cottony-white semi-solid mass suspended in the clear toluene phase. 110 ml of additional water was rinsed through the funnel and into the reactor over 15 minutes at 50° C. The reaction mixture was stirred for 35 minutes at 68°–70° C. The sodium hydroxide addition funnel was replaced with a funnel containing 67 grams (0.48 mole) of 97% sulfur monochloride and 70 ml of dry toluene. After cooling the reactor to 20° C., the sulfur monochloride/toluene solution was added over 25 minutes, allowing the temperature to rise to 35° C. The temperature was increased to 40° C. and after an additional 45 minutes raised to 50°–60° C. Stirring was stopped and the lower aqueous phase was allowed to separate and then drained. The organic phase was washed with 300 ml of water. Next, the organic phase was washed with 300 ml of water containing 2 ml of concentrated hydrochloric acid (pH of separated wash equaled 1), followed by 300 ml of water. The organic phase was drained into a beaker and mixed with 900 ml hexane, causing the product to precipitate. After cooling the slurry to room temperature, the solids were filtered, washed with 150 ml hexane and dried in an air oven at 50° C. 180.6 grams of N,N'-dimethyl-N,N'-dithiobis(benzenesulfonamide) were obtained. The product had a melting point of 101°–106° C. and a purity of 92–93 weight percent.

EXAMPLE 3
Preparation of N,N'-dimethyl-N,N'-dithiobis(benzenesulfonamide) by the Simultaneous Addition of Caustic and Sulfur Monochloride The reaction vessel was a 30 gallon glass-lined reactor equipped with a water jacket, bottom drain, agitator, thermocouple and two charge tanks. 16.6 kg of N-methyl-benzenesulfonamide and 33.1 kg of dry toluene were charged to the reactor and agitated for 5 minutes. 11.0 kg of 35% sodium hydroxide were charged to charge tank 1. A solution of premixed sulfur monochloride (6220 grams) and dry toluene (3269 grams) was charged to charge tank 2. The caustic solution in charge tank 1 was initiated to the reactor at a flow rate of 182 grams per minute. After 5 minutes the sulfur monochloride solution of charge tank 2 was introduced to the reactor at a flow rate of 155 grams per minute. The preceding flow of caustic solution insured the reaction mixture remains basic at all times. The reactor temperature was maintained below 50° C. with cooling water on the jacket. Upon introduction of a total charge of 11.0 kg of caustic solution which was introduced over the period of one hour and a total charge of 9352 grams of sulfur monochloride, the reaction mixture was agitated at 50° C. for 30 minutes. 9752 grams of water were charged to the reactor and the reaction mixture agitated for five minutes. The agitator was stopped and the pH of the lower aqueous phase was checked. The pH of the reaction mixture was adjusted to a range of from about 4 to 5 with hydrochloric acid. The reaction was agitated and heated to a temperature of 60° C. After the temperature reached 60° C., the agitation was stopped to allow the phases to separate for 5 minutes. The lower aqueous phase was decanted. The organic phase was agitated and cooled to 10° C. at a rate of 1° C./minute. After reaching 10° C., the reactor contents were centrifuged and the wet solids were air dried at 50° C. under vacuum. The filtrate was saved. 15.7 kg of product were recovered having the purity of 99.4% and a yield of 82.6%. The product had a melting point of 114°–117° C.

EXAMPLES 4–7
Preparation of N,N'-dimethyl-N,N'-dithiobis(benzenesulfonamide) by Using Recycled Organic Phase The recycle reactions were conducted according to the general procedure of Example 3 except that 90% by weight of the organic phase from the previous batch was charged to the reactor. Fresh toluene was also charged to the reactor to give 80 pounds of total solvent (recycle plus fresh). Next, 36.6 lbs. (16.62 kg) of N-methyl-benzenesulfonamide were charged. The reaction mixture was agitated for 5 minutes. 17.5 lbs. (7945 g) of sodium hydroxide and 7.2 lbs. (3269 g) of water were added to charge tank 1. 14.0 lbs. (6356 g) sulfur monochloride and 7.2 lbs. (3269 g) dry toluene were mixed and added to charge tank 2. The caustic flow to the reactor was started at a flow rate of 187 g/min. A total of 11.21 kg of 35% NaOH was added to the reactor over a period of 1 hour. Five minutes after the NaOH flow was initiated to the reactor, the sulfur monochloride flow was initiated at a rate of 159 g/min. A total of 9534 g of a sulfur monochloride solution was added over a period of 1 hour. After all the sulfur monochloride solution was added, 1 lb. (454 g) of dry toluene was used to flush the lines to insure that all the sulfur monochloride was charged. The reactor temperature was maintained below 50° C. with cooling water on the jacket. After all the reactants were added, the reactants were agitated at 50° C. for 30 minutes. After 30 minutes, 22.1 lbs. (10.03 kg) of water were charged to the reactor. The reaction mixture was agitated for 5 minutes. The pH of the lower aqueous phase was checked and adjusted to a range of from 4 to 5 with 31% HCl. The temperature of the reaction was raised to 60° C. The agitation was stopped after the temperature reached 60° C. and the phases were allowed to separate for 5 minutes. The lower aqueous phase was decanted and discarded. The agitator was started and the organic phase cooled to 10° C. at a rate of 1° C./min. After the reaction mixture reached 10° C., the reactor was drained and the contents were centrifuged. The filtrate was saved for recycle to next batch. The wet solids were dried overnight under vacuum at 50° C.

Table I below is a summary of the charges and products from the four recycle runs. All amounts in Table I are expressed in pounds. Table II below lists the results of HPLC analysis of the final product.

TABLE I
Summary of Charges & Products from Recycle Runs

| Example | 4 | 5 | 6 | 7 |
|---|---|---|---|---|
| Fresh toluene | 5.8 | 2.0 | 0.0 | 0.0 |
| Recycle toluene | 75.5 | 82.0 | 85.0 | 60.2 |
| MSA[1] | 36.6 | 36.6 | 36.6 | 25.9 |
| 35% NaOH | 24.7 | 24.7 | 24.7 | 17.5 |
| $S_2Cl_2$ | 13.8 | 13.8 | 13.8 | 9.9 |
| Diluent toluene[2] | 7.2 | 7.2 | 7.2 | 3.5 |
| Water | 22.1 | 22.1 | 22.1 | 15.6 |
| 31% HCl | 1.4 | 1.2 | 0.9 | 0.7 |
| Total toluene filtrate | 91.0 | 94.5 | 92.5 | 67.0 |
| Purge[3] | 9.0 | 9.5 | 9.3 | — |
| DMDTBS[4] | 35.3 | 35.6 | 36.6 | 25.8 |

[1] N—methyl-benzenesulfonamide
[2] Diluent toluene for $S_2Cl_2$
[3] Filtrate removed before recycle
[4] Product N,N'—dimethyl-N,N'—dithiobis (benzenesulfonamide)

TABLE II
Product Summary for Examples 4-7

| Example | 4 | 5 | 6 | 7 |
|---|---|---|---|---|
| Melting Point (°C.) | 114–117 | 113–116 | 114–117 | 113–116 |
| % MSA[1] (by wgt) | 1.24 | 0.98 | 1.30 | 1.08 |
| % DMDTB[2] (by wgt) | 98.6 | 99.0 | 97.9 | 98.5 |
| Yield (%) | 84.4 | 85.2 | 87.6 | 87.2 |

[1] N—methyl-benzenesulfonamide
[2] N,N'—dimethyl-N,N'—dithiobis (benzenesulfonamide)

EXAMPLES 8-14

Preparation of N,N'-dimethyl-N,N'-dithiobis(benzenesulfonamide)

A series of examples were conducted according to the following procedure. The reactions were conducted in a 30 gallon glass-lined reactor equipped with a water jacket, bottom drain, agitator, stripping column, vacuum line and thermocouple. Toluene and N-methylbenzenesulfonamide were charged to the reactor. The mixture was agitated for 5 minutes to dissolve the N-methyl-benzene- sulfonamide in the toluene. Next, a 34 weight percent aqueous solution of sodium hydroxide was added to the reactor over 30 minutes while maintaining the temperature below 50° C. A small amount of water was then charged to flush the lines of any residual sodium hydroxide. The temperature was raised to 70° C. and held for 30 minutes and then to 85° C. for another 5 minutes. At this point, the reactor contained a very thick slurry of white solids. The temperature was lowered to 25° C. in preparation for the sulfur monochloride addition. Toluene and sulfur monochloride were simultaneously charged to the reactor over 30–40 minutes. The sulfur monochloride was pumped with a Masterflex ® Peristaltic pump from a drum placed on a scale. The toluene was pressured in from a charge tank through a rotometer. The two materials were mixed in-line before entering the reactor through a dip-tube in the vapor phase. The reaction temperature was maintained near 40° C. with cooling water on the jacket during the sulfur monochloride addition. After the addition was complete, the mixture was agitated at 40° C. for 45 minutes and then at 55° C. for 5 minutes. The washing procedure was started by initially adding water to the reactor in order to dissolve the salts formed by the reaction. At this point, two immiscible liquid phases were present. The lower aqueous phase, containing most of the salts, was decanted and discarded. The upper organic phase was neutralized with 25% HCl and then water washed three times. After the final wash and decant, the precipitation was initiated. First, approximately ½ of the toluene was stripped from the solution at about 45° C. and 25 inches of vacuum. This precipitated some of the product, N,N'-dimethyl-N,N'-dithiobis(-benzenesulfonamide), and gave a slurry of the product in toluene. Next, the slurry temperature was lowered to 30° C. Hexane was added to the reactor with agitation to precipitate the remaining product. The slurry was drained from the reactor and centrifuged in a basket centrifuge. The wet cake was then reslurried in isopropyl alcohol. The isopropyl alcohol/N,N'-dimethyl-N,N'-dithiobis (benzenesulfonamide) slurry was centrifuged and the wet solids were dried overnight in a vacuum dryer at 50° C. The dried product was a white, crystalline solid. Table III below lists the charge and product quantities used in each of the seven examples.

TABLE III

| Example | 8 | 9 | 10 | 11 | 12 | 13 | 14 |
|---|---|---|---|---|---|---|---|
| MSA[1] (lbs.) | 41.5 | 41.5 | 41.5 | 41.5 | 41.5 | 41.5 | 39.6 |
| Toluene Charge (lbs.) | 91.0 | 91.0 | 91.0 | 91.0 | 91.0 | 91.0 | 87.0 |
| 34% NaOH Charge (lbs.) | 28.4 | 29.3 | 29.3 | 29.3 | 29.5 | 29.5 | 27.6 |
| $S_2Cl_2$ Charge (lbs.) | 15.7 | 16.0 | 16.2 | 16.2 | 16.0 | 16.2 | 15.3 |
| Diluent Toluene (lbs.) | 22.0 | 22.0 | 17.0 | 17.0 | 17.0 | 17.0 | 17.0 |
| Wash #1 (lbs. water) | 118.0 | 115.0 | 115.0 | 115.0 | 115.0 | 115.0 | 115.0 |
| 38% HCl Charge (lbs.) | 0.26 | 0.20 | 0.20 | 0.20 | 0.20 | 0.20 | 0.19 |
| Wash #2 (lbs. water) | 70.0 | 70.0 | 70.0 | 70.0 | 70.0 | 70.0 | 70.0 |
| Wash #3 (lbs. water) | 70.0 | 70.0 | 70.0 | 70.0 | 70.0 | 70.0 | 70.0 |
| Wash #4 (lbs. water) | 70.0 | 70.0 | 70.0 | 70.0 | 70.0 | 70.0 | 70.0 |
| Stripped Toluene (lbs.) | 77.5 | 70.0 | 72.0 | 73.0 | 66.8 | 67.5 | 70.0 |
| Hexane Charge (lbs.) | 75.0 | 68.0 | 68.0 | 68.0 | 75.5 | 75.0 | 67.0 |
| IPA[2] Wash (lbs.) | 50.0 | 60.0 | 60.0 | 60.0 | 59.0 | 60.0 | 60.0 |
| Dry Product (lbs.) | 31.0 | 37.3 | 37.7 | 38.3 | 40.0 | 39.0 | 37.5 |
| Crude Yield | 66.1% | 79.5% | 80.4% | 81.7% | 85.3% | 83.2% | 84.0% |

[1] N—methyl-benzenesulfonamide
[2] Isopropyl alcohol

While certain representative embodiments and details have been shown for the purpose of illustrating the invention, it will be apparent to those skilled in this art that various changes and modifications may be made therein without departing from the spirit or scope of the invention.

What is claimed is:

1. A process for synthesizing N,N'-dithiobis(sulfonamides) comprising reacting a sulfonamide of the formula:

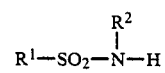

$$R^1-SO_2-\underset{\underset{H}{|}}{\overset{\overset{R^2}{|}}{N}}$$

with sulfur monochloride and caustic in a mixed organic-aqueous media, wherein $R^1$ and $R^2$ are independently selected from the group consisting of alkyl radicals having 1 to 20 carbon atoms, cycloalkyl radicals having 5 to 20 carbon atoms, phenyl radicals and alkaryl radicals having 7 to 20 carbon atoms, and haloaryl radicals having about 6 to about 10 carbon atoms and where $R^1$ is also selected from radicals having the formula:

wherein $R^3$ and $R^4$ are individually selected from said alkyl, cycloalkyl, phenyl, alkaryl and haloaryl radicals and wherein $R^3$ and $R^4$ can be joined together to represent radicals selected from $-(CH_2)_n-$, where n is an integer of 4 to 7 and $-(CH_2)_2-O-(CH_2)_2-$.

2. The process of claim 1 wherein the organic media is selected from the group consisting of benzene, chlorobenzenes, toluene, ethylbenzene, n-propylbenzene, isobutylbenzene, xylene, and mixtures thereof.

3. The process of claim 2 wherein the organic media is selected from the group consisting of benzene, toluene, xylene, and mixtures thereof.

4. The process of claim 1 wherein the weight ratio of organic to aqueous media is from about 7:1 to about 1:1.

5. The process of claim 1 wherein said caustic is selected from the group consisting of sodium hydroxide, potassium hydroxide or mixtures thereof.

6. The process of claim 5 wherein said caustic is introduced to the reactor at a rate so as to be present in sufficient excess of sulfur monochloride to maintain an alkaline pH throughout the course of the reaction and in the final reaction mixture.

7. The process of claim 1 wherein $R^1$ is selected from the group consisting of phenyl or tolyl radicals and $R^2$ is selected from the group consisting of alkyl radicals having from 1 to 4 carbon atoms.

8. The process of claim 1 wherein said caustic is an aqueous solution of sodium hydroxide, potassium hydroxide or mixtures thereof.

9. The process of claim 1 wherein said N,N'-dithiobis(sulfonamide) is N,N'-dimethyl-N,N'-dithiobis(p-toluenesulfonamide).

10. The process of claim 1 wherein said N,N'-dithiobis(sulfonamide) is N,N'-dimethyl-N,N'-dithiobis(benzenesulfonamide).

11. The process of claim 1 wherein said caustic and sulfur monochloride are simultaneously introduced to the reactor.

12. The process of claim 11 wherein the product is removed from solution by cooling to precipitate.

13. The process of claim 1 wherein all of said caustic is added to the reactor with said sulfur monochloride being added later to said reactor.

14. The process of claim 13 wherein the product is removed from solution by precipitation by addition of a non-solvent.

* * * * *